(12) United States Patent
Tuseth et al.

(10) Patent No.: US 10,537,670 B2
(45) Date of Patent: Jan. 21, 2020

(54) VENTRICULAR ASSIST DEVICE AND METHOD

(71) Applicant: NUHEART AS, Bergen (NO)

(72) Inventors: Vegard Tuseth, Bergen (NO); Shawn Patterson, Minneapolis, MN (US); Philip J. Haarstad, Chanhassen, MN (US); Knut Klepsvik, Kolltveit (NO)

(73) Assignee: NUHEART AS, Bergen (NO)

( * ) Notice: Subject to any disclaimer, the term of this patent is extended or adjusted under 35 U.S.C. 154(b) by 0 days.

(21) Appl. No.: 15/582,037

(22) Filed: Apr. 28, 2017

(65) Prior Publication Data

US 2018/0311421 A1    Nov. 1, 2018

(51) Int. Cl.
*A61M 1/10*    (2006.01)
*A61M 1/12*    (2006.01)

(52) U.S. Cl.
CPC ........... *A61M 1/1008* (2014.02); *A61M 1/122* (2014.02)

(58) Field of Classification Search
CPC .......................... A61M 1/1008; A61M 1/1031
USPC .......................................................... 600/16
See application file for complete search history.

(56) References Cited

U.S. PATENT DOCUMENTS

| | | |
|---|---|---|
| 5,571,215 A | 11/1996 | Sterman et al. |
| 5,728,122 A | 3/1998 | Leschinsky et al. |
| 5,921,913 A | 7/1999 | Siess |
| 6,134,467 A | 10/2000 | Ouchi |
| 6,196,230 B1 | 3/2001 | Hall et al. |
| 6,425,916 B1 | 7/2002 | Garrison et al. |
| 7,295,878 B1 | 11/2007 | Meadows et al. |
| 7,878,967 B1 | 2/2011 | Khanal |
| 7,942,804 B2 | 5/2011 | Khaw |
| 8,157,852 B2 | 4/2012 | Bloom et al. |
| 8,738,147 B2 | 5/2014 | Hastings et al. |
| 9,314,556 B2 | 4/2016 | Tuseth |
| 9,539,378 B2 | 1/2017 | Tuseth |
| 10,130,742 B2 | 11/2018 | Tuseth |
| 2001/0047150 A1 | 11/2001 | Chobotov |
| 2002/0082584 A1 | 6/2002 | Rosenman et al. |
| 2002/0099396 A1 | 7/2002 | Slaker et al. |
| 2002/0173742 A1 | 11/2002 | Keren et al. |
| 2002/0173817 A1 | 11/2002 | Kletschka et al. |
| 2003/0100920 A1 | 5/2003 | Akin et al. |
| 2003/0181843 A1 | 9/2003 | Bibber et al. |
| 2003/0233143 A1 | 12/2003 | Gharib et al. |
| 2004/0006305 A1 | 1/2004 | Hebert et al. |
| 2004/0097973 A1 | 5/2004 | Loshakove et al. |
| 2004/0098081 A1 | 5/2004 | Landreville et al. |
| 2004/0236170 A1 | 11/2004 | Kim |
| 2004/0243051 A1 | 12/2004 | Monzyk et al. |

(Continued)

FOREIGN PATENT DOCUMENTS

AU    2014201432 A1    10/2014
EP    1907028 A1    4/2008

(Continued)

*Primary Examiner* — Nadia A Mahmood
(74) *Attorney, Agent, or Firm* — Baker & Hostetler LLP

(57) ABSTRACT

An intracorporeal device is provided for supporting heart function of a patient. The intracorporeal device is configured to be secured across at least two anatomical walls of the heart. The intracorporeal device is configured to be secured to one or more anatomical walls by a connector. The connector is arranged to be positioned across one or more anatomical walls.

30 Claims, 9 Drawing Sheets

(56) References Cited

U.S. PATENT DOCUMENTS

| | | |
|---|---|---|
| 2005/0075696 A1 | 4/2005 | Forsberg et al. |
| 2005/0165344 A1 | 7/2005 | Dobak |
| 2005/0187425 A1 | 8/2005 | Alferness et al. |
| 2006/0079736 A1 | 4/2006 | Chin et al. |
| 2006/0089707 A1 | 4/2006 | Vassiliades et al. |
| 2006/0155158 A1 | 7/2006 | Aboul-Hosn |
| 2007/0249985 A1 | 10/2007 | Brenneman et al. |
| 2008/0195226 A1 | 8/2008 | Williams et al. |
| 2008/0300574 A1 | 12/2008 | Belson et al. |
| 2009/0088597 A1 | 4/2009 | Frazier et al. |
| 2009/0093670 A1 | 4/2009 | Annest et al. |
| 2009/0093751 A1 | 4/2009 | Tao et al. |
| 2009/0105654 A1 | 4/2009 | Kurth et al. |
| 2009/0182188 A1 | 7/2009 | Marseille et al. |
| 2009/0228078 A1 | 9/2009 | Zhang et al. |
| 2010/0191035 A1 | 7/2010 | Kang et al. |
| 2010/0268316 A1 | 10/2010 | Brenneman et al. |
| 2010/0331972 A1 | 12/2010 | Pintor et al. |
| 2011/0130619 A1 | 6/2011 | Whisenant et al. |
| 2011/0184224 A1 | 7/2011 | Garrigue |
| 2011/0196190 A1 | 8/2011 | Farnan et al. |
| 2011/0230821 A1* | 9/2011 | Babic ............... A61M 25/1011 604/28 |
| 2011/0234155 A1 | 9/2011 | Chen et al. |
| 2011/0257723 A1 | 10/2011 | McNamara |
| 2011/0276075 A1 | 11/2011 | Fung et al. |
| 2011/0306916 A1 | 12/2011 | Nitzan et al. |
| 2012/0053657 A1 | 3/2012 | Parker et al. |
| 2012/0059459 A1 | 3/2012 | Asirvatham et al. |
| 2012/0139355 A1 | 6/2012 | Ganem et al. |
| 2012/0146575 A1 | 6/2012 | Armstrong et al. |
| 2012/0150259 A1 | 6/2012 | Meskens |
| 2012/0165928 A1 | 6/2012 | Nitzan et al. |
| 2012/0172654 A1 | 7/2012 | Bates |
| 2012/0172655 A1 | 7/2012 | Campbell et al. |
| 2012/0178985 A1 | 7/2012 | Walters et al. |
| 2012/0232316 A1 | 9/2012 | Nappa |
| 2012/0245649 A1 | 9/2012 | Bohori et al. |
| 2012/0259263 A1 | 10/2012 | Celermajer et al. |
| 2012/0265003 A1 | 10/2012 | Dambrosio et al. |
| 2012/0301318 A1 | 11/2012 | Er |
| 2013/0060267 A1 | 3/2013 | Farnan et al. |
| 2013/0127253 A1 | 5/2013 | Stark et al. |
| 2013/0193914 A1 | 8/2013 | Gaddam et al. |
| 2013/0301318 A1 | 11/2013 | Asako et al. |
| 2014/0005466 A1 | 1/2014 | Crosby et al. |
| 2014/0031607 A1 | 1/2014 | Zilbershlag et al. |
| 2014/0236123 A1 | 8/2014 | Birmingham et al. |
| 2014/0287274 A1 | 9/2014 | Hwang |
| 2014/0336445 A1 | 11/2014 | Farnan et al. |
| 2015/0005570 A1 | 1/2015 | Fritz et al. |
| 2015/0119633 A1 | 4/2015 | Haselby et al. |
| 2015/0223839 A1 | 8/2015 | Spence et al. |
| 2015/0250935 A1 | 9/2015 | Anderson et al. |
| 2015/0258260 A1* | 9/2015 | Tuseth ............... A61B 17/3478 600/16 |
| 2015/0258312 A1 | 9/2015 | Tuseth |
| 2015/0335801 A1 | 11/2015 | Farnan et al. |
| 2016/0022896 A1 | 1/2016 | Burkhoff |
| 2016/0175501 A1 | 6/2016 | Schuermann |
| 2017/0000935 A1 | 1/2017 | Vasilyev et al. |
| 2017/0043077 A1 | 2/2017 | Tuseth et al. |
| 2017/0047762 A1 | 2/2017 | Tuseth et al. |
| 2017/0106176 A1 | 4/2017 | Taft et al. |
| 2017/0189063 A1 | 7/2017 | Tuseth et al. |
| 2017/0189650 A1 | 7/2017 | Tuseth et al. |
| 2017/0196565 A1 | 7/2017 | Tuseth et al. |
| 2017/0197019 A1 | 7/2017 | Tuseth et al. |
| 2017/0216029 A1 | 8/2017 | Crowley et al. |
| 2018/0098847 A1 | 4/2018 | Tuseth et al. |

FOREIGN PATENT DOCUMENTS

| | | |
|---|---|---|
| EP | 2338540 A1 | 6/2011 |
| GB | 2504176 A | 1/2014 |
| JP | 2008545083 A | 12/2008 |
| JP | 2012523894 A | 10/2012 |
| WO | 2000027312 | 5/2000 |
| WO | 2001078580 | 10/2001 |
| WO | 2005037345 A2 | 4/2005 |
| WO | 2007003351 A1 | 1/2007 |
| WO | 2008027869 A2 | 3/2008 |
| WO | 2008055301 A1 | 5/2008 |
| WO | 2008106717 A1 | 9/2008 |
| WO | 2008134267 A2 | 11/2008 |
| WO | 2009134471 A1 | 11/2009 |
| WO | 2010042056 A1 | 4/2010 |
| WO | 2010114666 A1 | 10/2010 |
| WO | 2010132451 A2 | 11/2010 |
| WO | 2011011787 A2 | 1/2011 |
| WO | 199727898 | 10/2012 |
| WO | 2013036588 A1 | 3/2013 |
| WO | 2013096965 A1 | 6/2013 |
| WO | 2015075576 A1 | 5/2015 |
| WO | 2015140179 A2 | 9/2015 |

\* cited by examiner

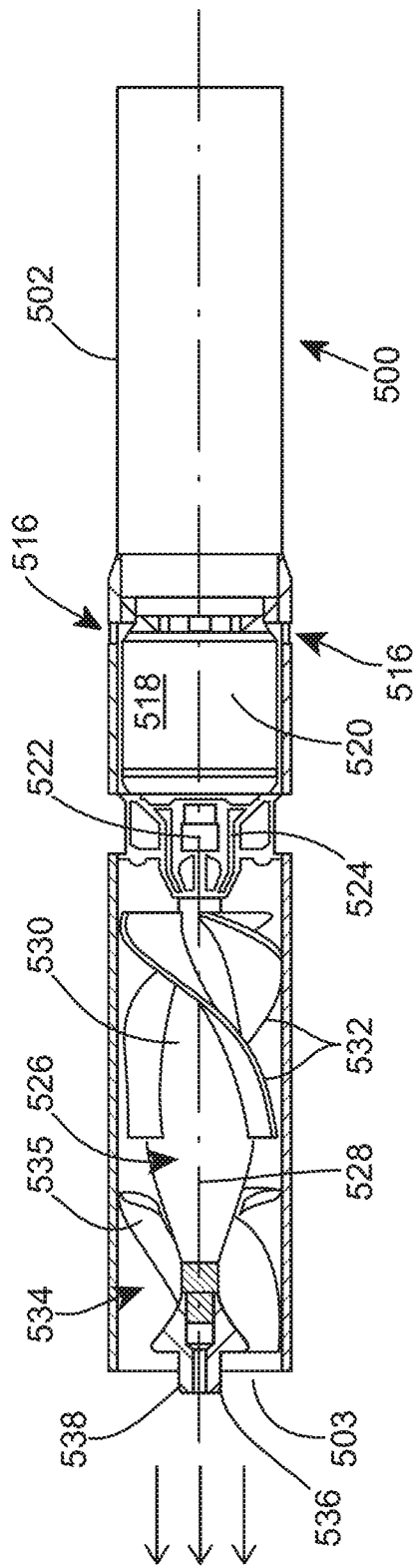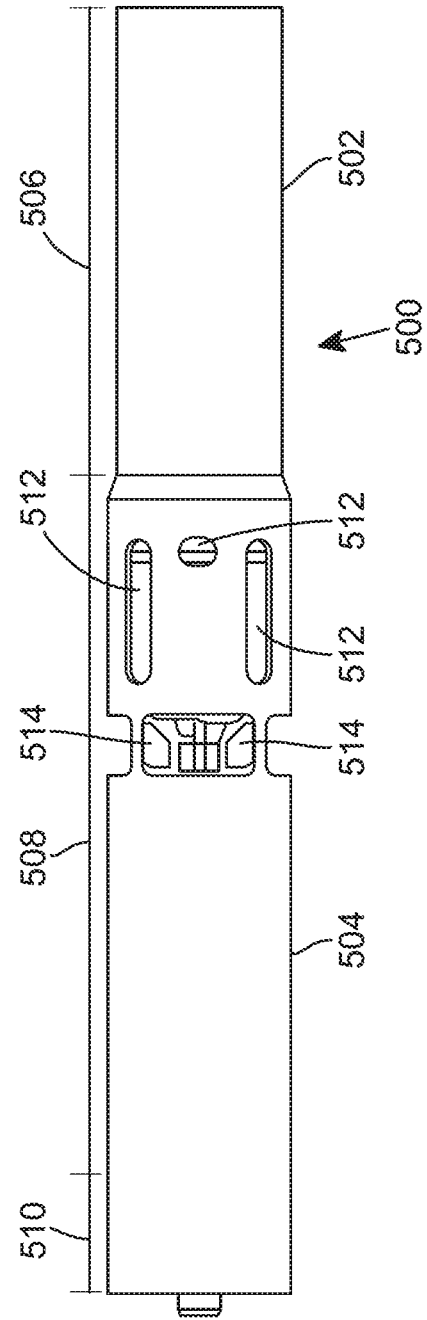

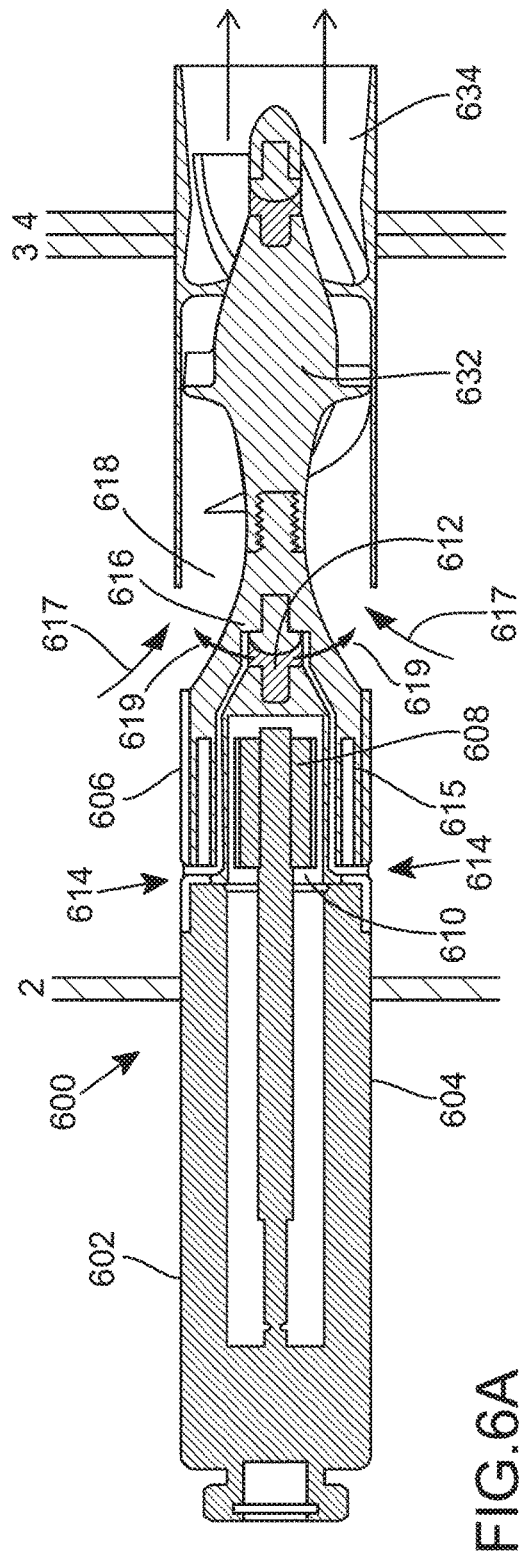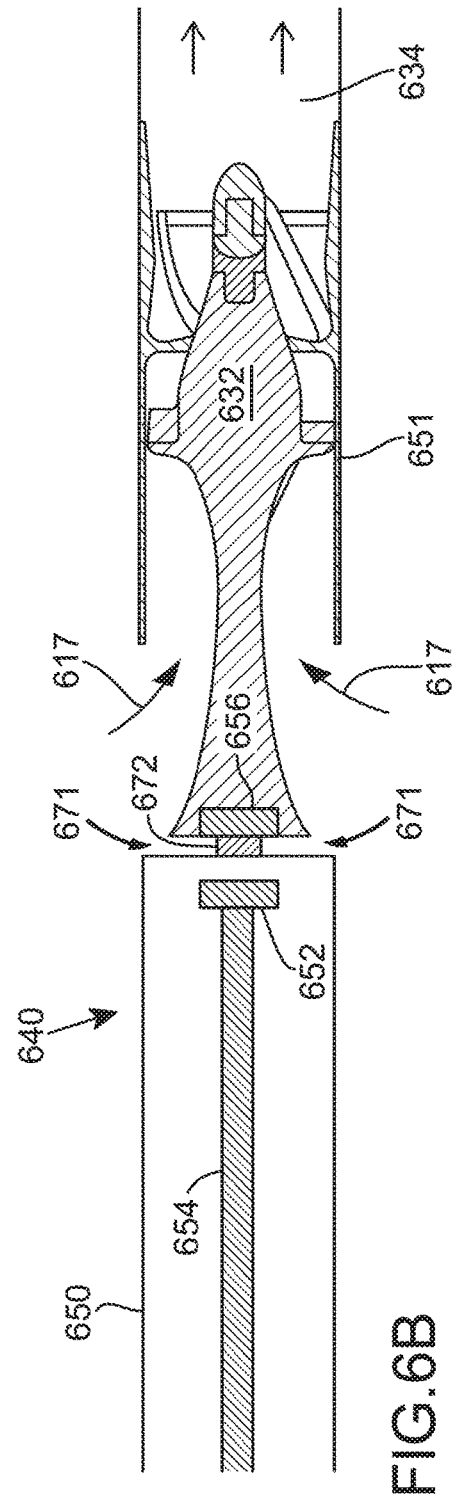

VENTRICULAR ASSIST DEVICE AND METHOD

FIELD OF THE INVENTION

The present invention generally relates to the field of medical devices and surgery devices. More specifically, the invention relates to a catheter and corresponding methods of use of the catheter. The present invention is particularly useful in the context of minimally invasive transcatheter and/or percutaneous procedures, such as those described in PCT Application No. PCT/EP2015/055578, entitled "PERCUTANEOUS SYSTEM, DEVICES AND METHODS" filed 17 Mar. 2015 and expressly incorporated herein by reference in its entirety.

BACKGROUND

In PCT/EP2015/055578, the Inventor describes an intracorporeal connector for fluid communication between a first and a second anatomical compartment, in particular a ventricular assist system for allowing blood flow between the left atrium and the aorta of a patient. The system is implanted across the roof of the left atrium and the aortic wall and generally comprises two main components, namely an anchor or connector element and a fluid regulation device such as a pump.

The ventricular assist system is preferably delivered and implanted using a transcatheter system as described for example in PCT Application No. PCT/EP2015/055578, or in PCT/EP2016/082889 entitled "TRANSCATHETER INSERTION SYSTEM" filed on 29 Dec. 2016; PCT Application No. PCT/EP2017/050275 entitled "CONNECTOR AND METHOD FOR COUPLING ANATOMICAL WALLS" filed on 6 Jan. 2017, and U.S. application Ser. Nos. 15/288,642 and 15/288,738 filed on 7 Oct. 2016, all incorporated herein by reference.

The connector element comprises a proximal portion, an intermediate portion and a distal portion. The proximal portion comprises a plurality of arms which, in a working configuration, lie against the wall of the first compartment; the intermediate portion comprises a fluid conduit and, in a working configuration, is positioned across the anatomical walls; the distal portion comprises a plurality of arms which, in a working configuration, lie against the aortic wall. The intermediate portion is adapted and configured to keep the two anatomical walls to remain in contact with each other; while the distal and proximal arms are adapted and configured to maintain the structural integrity of the anatomical walls. This is particularly important as the connector is adapted and configured to safely support the fluid regulation device across the anatomical walls, which will be under pressure and susceptible to dislodgment due to e.g. the structure of the fluid regulation device itself, blood flow created by the pump and patient movements.

While the above ventricular assist system can be safely implanted and fluid flow successfully established, the size and structure of the heart is such that there has been a need to adapt the fluid regulation device and consequently the delivery and implantation methods and systems. The fluid regulation device would typically comprise a pump element, a motor element, and optionally a battery element (as described for example in PCT Application No. PCT/EP2016/069159 filed on 11 Aug. 2016) and, if required, means for recharging said battery. Space and manipulation within the heart is limited and miniaturisation can only be considered insofar as the efficiency of the fluid regulation device is not negatively affected. As the size of the device increases, more pressure is exerted on the anatomical walls, the integrity of which could become compromised. There is therefore a risk of heart tissue trauma, which dangerous and potentially be lethal to the patient.

It is an object of this invention to mitigate problems such as those described above.

SUMMARY OF THE INVENTION

According to a first aspect, there is provided a method for supporting heart function of a patient comprising the step of securing an intracorporeal device across at least two anatomical walls of the heart, wherein at least one anatomical wall is an intra-cardiac wall and a least one anatomical wall is an extra-cardiac wall.

Thus, the intracorporeal device is safely secured to the heart using a two-point anchoring system. The device is stabilised and the pressure exerted by the device and blood flow onto the heart structure is shared so that the risk of strain and trauma to a single wall is reduced.

Within the context of the invention, "intracorporeal" means inside the patient's body and "extracorporeal" means outside the patient's body. For example, an intracorporeal device or component will be located within the patient's body, while an extracorporeal device or component will be located outside the patient's body.

Within the context of the invention, "intra-cardiac" means inside the heart and "extra-cardiac" means between the inside and the outside of the heart or outside the heart. For example, an intra-cardiac wall is an anatomical wall located inside the heart. Examples of intra-cardiac walls include, but are not limited to the atrial septum between the right and left atria and the interventricular septum between the right and left ventricles. An extra-cardiac wall can be an anatomical wall between the inside and the outside of the heart for example the wall between the inside of the left atrium, of the right atrium, of the left ventricle or of the right ventricle and the outside of the heart and also the aortic wall.

In a preferred embodiment, the intra-cardiac wall is the atrial septum and the extra-cardiac wall is the wall of the left atrium, most preferably, the roof of the left atrium. These anatomical walls are particularly advantageous when a fluid regulation device is to be implanted, which regulates the flow of fluid from the left atrium to the aorta. For example, in PCT/EP2015/055578, the fluid regulation device is inserted through a puncture through the atrial septum, then implanted across the roof of the left atrium so that blood flows through inlets positioned in the left atrium to outlets positioned in the aorta. The left atrium and aortic walls are subjected to tension due to the implantation of the fluid regulation device itself and to pressure due to the fluid flow. By providing a second anchoring point, e.g. across the atrial septum, the device is stabilised and the anatomical walls are individually subjected to less pressure. Thus, the risk of injury, trauma and leak is minimised. The atrial septum is preferred in that it is generally rigid and robust enough to secure and support an intracorporeal device but flexible enough to buffer for any movement during and post-implantation. In addition, the atrial septum is often used as an insertion path and can be used as a second anchoring point without the need for further puncture.

Preferably, the method further comprises the step of securing the intracorporeal device across at least a third anatomical wall. More preferably, the third anatomical wall is a wall adjacent to the extra-cardiac wall. Within the context of the invention, "adjacent wall" means a "wall naturally physically close". For example, two adjacent walls may be the adjacent walls of two adjacent anatomical compartments, such as the wall of the left atrium and the aortic wall. In a preferred embodiment, the third anatomical wall is the aortic wall adjacent to the roof of the left atrium.

The present invention is particularly useful when the flow of fluid is to be established between two anatomical compartments separated by at least two anatomical walls. As described in PCT/EP2015/055578, the anatomical walls are pushed into contact with each other by means of a delivery catheter or outer sheath, punctured and secured together for example using a connector. When two anchoring points are provided, the pressure and tension is spread and are no longer focussed on and around the connector.

Preferably, the intracorporeal device comprises a proximal portion intended to be positioned in a first anatomical compartment, an intermediate portion intended to be positioned in a second anatomical compartment, a distal portion intended to be positioned in a third anatomical compartment. In a preferred embodiment, the proximal portion of the intracorporeal device is intended to be positioned in the right atrium, the intermediate portion is intended to be positioned in the left atrium and the distal portion is intended to be positioned in the aorta. The intracorporeal device can therefore be secured to the atrial septum (between the proximal and the intermediate portion) and to the wall of the left atrium and aortic wall (between the intermediate portion and the distal portion).

The position of the various elements of the intracorporeal device may be adapted and configured to assist fluid flow between any two compartments as will be described below in more details. In a preferred embodiment, the intracorporeal device is a fluid regulation device for assisting fluid flow from the second to the third compartment, e.g. from the left atrium to the aorta.

Preferably, the intracorporeal device is secured to one or more anatomical walls by means of a connector. More preferably, the connector may be a separate connector or may be integrally formed or attached to the intracorporeal device.

Preferably, the connector comprises a neck intended to be positioned across one or more anatomical wall(s), a first plurality of arms extending from a first end of the neck, and a second plurality of arms extending from the second end of the neck. As described in the applicant's previous applications cited herein, the arms are preferably movable from a transcatheter delivery configuration (e.g. in line with the neck) to a working configuration (e.g. substantially perpendicular to the neck).

In the case of a separate connector, the connector and/or the intracorporeal device comprise means for coupling the intracorporeal device to the connector.

Preferably, the connector is integrally formed or coupled to the intracorporeal device. In this embodiment, the connector will comprise means for connecting the intracorporeal device to the anatomical wall(s). For example, the intracorporeal device may comprise a plurality of arms extending from the intracorporeal device. Preferably, the arms are preferably movable from a transcatheter delivery configuration (e.g. in line with the neck) to a working configuration (e.g. substantially perpendicular to the neck).

In a preferred embodiment, the intracorporeal device comprises a means for fixing the intracorporeal device to the connector. Preferably the fixing means comprises a plurality of arms extending from the intracorporeal device, preferably the distal end of the intracorporeal device. The arms may be moved from delivery configuration (e.g. extending substantially longitudinally from the intracorporeal device) to a working configuration (e.g. extending away from the longitudinal axis of the intracorporeal device). In the working configuration, the fixing arms may cooperate with the connector to anchor the intracorporeal device to the anatomical walls. In addition, the fixing arms may serve as additional support to the wall tissue, against the fluid flow and/or the intracorporeal device's own weight and bulk.

Preferably, the intracorporeal device comprises one or more recesses adapted and configured to receive one or more anatomical walls. In a preferred embodiment, the intracorporeal device comprises an elongated housing or a substantially cylindrical housing. The intracorporeal device may comprise a circumferential recess adapted to receive the anatomical wall(s) therein, thereby securing the intracorporeal device to the wall. Preferably, to facilitate the insertion of the anatomical wall(s) into the recesses, the recesses have slopped or curved walls.

According to a second aspect of the invention, there is provided an intracorporeal device for supporting heart function of a patient, wherein said device is adapted and configured to be secured across at least two anatomical walls of the heart.

Preferably, the at least one anatomical wall is an intracardiac wall and a least one anatomical wall is an extracardiac wall.

Preferably, the intracorporeal device is adapted and configured to be secured to one or more anatomical walls by means of a connector, said connector being integrally formed or coupled to the intracorporeal device.

Preferably, the intracorporeal device is adapted and configured to be secured to one or more anatomical walls by means of a connector and a fixing means, said connector being arranged to be positioned across one or more anatomical walls and said fixing means being integrally formed or coupled to the intracorporeal device.

Preferably, the fixing means comprises a plurality of arms extending from the intracorporeal device, for example the distal end of the intracorporeal device.

Preferably, the intracorporeal device comprises one or more recesses adapted and configured to receive one or more anatomical walls.

Preferably, the intracorporeal device comprises a proximal portion intended to be positioned in a first anatomical compartment, an intermediate portion intended to be positioned in a second anatomical compartment, a distal portion intended to be positioned in a third anatomical compartment.

Preferably, the intracorporeal device comprises a motor located in the proximal portion. Preferably, the intracorporeal device comprises one or more fluid inlet ports in the intermediate portion. Preferably, the intracorporeal device comprises a pump in the intermediate portion.

Preferably, the pump comprises an impeller and a pump housing, wherein the impeller is positioned within the pump housing. The impeller is a rotatable element that accelerates fluid outwards from the centre of rotation in a direction parallel to the impeller's major (longitudinal) axis, which is generally referred to as an axial flow impeller. The impeller rotates about its major axis with respect to the pump housing. The impeller is surrounded by the pump housing so that the rotational velocity of the impeller transfers into pressure when the outward movement of the fluid is confined by the pump housing.

Preferably, the impeller comprises a tapered profile. The tapered profile increases from the proximal portion end to a mid portion of the impeller, wherein the tapered profile then decreases towards the distal portion end such that the cross section of the tapered impeller approximates an ellipse, wherein the major axis of the ellipse is parallel to the major axis of the pump housing. The tapered profile of the impeller has an advantage of increasing fluid pressure in the pump housing. Thus fluid, such as blood, spends less time around parts of the device that generate heat, such as the motor and various bearings within the intracorporeal device. This reduces the probability of the fluid being damaged by heat generated by the device, which in turn reduces the probability of the fluid clotting and blocking the circulatory system. Thus fluid cools the surface of the motor housing and the internal pump elements.

Preferably, the intracorporeal device comprises one or more fluid outlet ports in the distal portion. One or more fluid inlet ports may be positioned in the proximal and/or intermediate portion depending on the compartments the fluid flows from/to. In a preferred embodiment, the proximal portion of the intracorporeal device is intended to be positioned in the right atrium, the intermediate portion is intended to be positioned in the left atrium, and the distal portion is intended to be positioned in the aorta. In a most preferred embodiment, the intermediate portion comprises one or more inlet ports and the distal portion comprises one or more outlet ports so that fluid can flow from the left atrium to the aorta.

Preferably, the length of the intermediate portion and the distal portion is designed such that the one or more fluid inlet ports in the intermediate portion are positioned in the left atrium and the one or more fluid outlet ports in the distal portion are positioned in the aorta.

Preferably, the intracorporeal device comprises a static diffuser positioned in the distal portion of the intracorporeal device. Preferably, the diffuser is positioned between the impeller and the one or more fluid outlet ports. Preferably, the diffuser is coupled to an end of the impeller via a bearing. Preferably, the diffuser is fixedly attached to the interior of the pump housing such that the diffuser is not able to rotate. Preferably, the diffuser and bearing support the impeller and allow the impeller to rotate about its major axis, whilst the diffuser remains fixed to the interior of the pump housing. The diffuser has an advantage of increasing fluid diffusion from the outlet of the device due to the angle and profile of the blades of the diffuser.

Preferably, the intracorporeal device comprises a fixing means that is arranged to secure the intracorporeal device to an anatomical wall. Preferably, the fixing means is at an end of the distal portion of the intracorporeal device.

Preferably, in use, the connector is positioned through the roof of the left atrium and the aortic wall. Preferably, the neck of the connector and/or the distal portion of the intracorporeal device form a pericardial seal. Preferably, the neck of the connector acts as a docking means to assist in coupling the distal portion of the intracorporeal device across the anatomical walls and with respect to the connector.

The fixing means may be a type of anchor/support member with a number of arms/tissue support members that can deploy against the wall of the aorta for example. This may position and secure the distal portion of the device with respect to the aorta to allow for efficient fluid transfer through the device.

Preferably, the intracorporeal device comprises a static diffuser positioned at an end of the distal portion. This has the advantage of further increasing fluid diffusion at an outlet of the device because the fixed blades aid in fluid diffusion. This also has the advantage of facilitating easier deployment of the device because a guide wire and/or balloon may be attached to a guide wire holder on the static diffuser to enable accurate positioning within the human body.

Preferably, the intracorporeal device comprises a motor coupling element that is arranged to couple a drive shaft of the motor to the pump. Preferably, the motor coupling element is positioned between the motor and the impeller. Preferably, the motor coupling element magnetically couples the drive shaft of the motor to the pump. This has an advantage of maintaining a hermetic seal of the motor and drive shaft with respect to fluid within the circulatory system, whilst also enabling the motor and drive shaft to be easily removed from the remainder of the intracorporeal device. Thus components of the intracorporeal device that are most likely to need removal, modification or replacement, e.g. the motor, can be detached and replaced easily whilst maintaining the remainder of the intracorporeal device in position within the body.

Preferably, the motor coupling element axially couples the drive shaft of the motor to the pump. This has an advantage of simplifying the coupling between the drive shaft of the motor and the pump, whilst maintaining a hermetic seal between the motor and fluid within the body.

Preferably, the motor coupling element radially couples the drive shaft of the motor to the pump. Preferably, a portion of the motor coupling element surrounds and magnetically couples to an elongate portion of the motor that houses the motor drive shaft. This has an advantage of increasing the torque transfer between the drive shaft and the pump impeller. Radial configuration of the coupling magnet forces eliminates additional bearing loading and heat generated by friction.

Preferably, the motor, the drive shaft, and a magnetic element at an end of the drive shaft are situated in a hermetically sealed housing. This has an advantage of allowing the motor to be positioned in the circulatory system. If the elements discussed above were not situated in a hermetically sealed housing, fluid within the circulatory system would damage these elements and/or the elements may cause contamination to the fluid within the circulatory system.

Preferably, a portion of the motor coupling element partially surrounds a portion of the hermetically sealed housing containing the magnetic element. This has an advantage of facilitating radial magnetic coupling and allowing fluid to flow between the motor coupling element and the portion of the hermetically sealed housing.

Preferably, an interstitial space/void is present between the portion of the motor coupling element and the portion of the hermetically sealed housing. This has an advantage of facilitating fluid flow in the interstitial space to prevent fluid damage.

Preferably, an interface of the motor coupling element is magnetically fixable to an interface of the motor in order to couple the motor drive shaft to the pump, and wherein a fluid inlet is defined between said interfaces during coupling. This has an advantage of facilitating fluid flow between the interfaces so that fluid can enter the interstitial space between the interfaces.

Preferably, a further interface of the motor coupling element couples to an interface of the impeller. This has an advantage of translating movement of the motor drive shaft to the impeller.

Preferably, the motor coupling element comprises one or more bore portions. This has an advantage of allowing fluid that has entered the interstitial spaces to exit the motor coupling element. This results in washing of a bearing inside of the motor coupling element, without the fluid temperature increasing to a point where the fluid becomes damaged.

Preferably, the one or more bore portions are bore holes and/or segmented arms that couple the interfaces of the motor coupling element to the respective impeller interfaces.

Preferably, in use, fluid is arranged to flow between the motor interface and the interface of the motor coupling element and through the one or more bore portions towards the impeller. This has an advantage of reducing heat in the bearing and preventing the fluid from being damaged by excess heat.

Preferably, the one or more fluid inlet ports are positioned between the one or more bore portions and the impeller in the intermediate portion of the pump housing. This has an advantage of allowing fluid exiting from the bore portions to mix with fluid entering the fluid inlet ports. Thus any excess heat absorbed by the fluid exiting the bore portions can be dissipated efficiently with fluid entering via the fluid inlet ports.

Preferably, the intracorporeal device comprises power and control means. Preferably, the control means is coupled to the motor via a tapered portion. The tapered portion has an advantage of reducing strain on the connector between the motor and the power and control means. Preferably, the tapered portion reduces in dimension as it tapers away from the proximal portion of the intracorporeal device.

Within the context of the invention, the terms "proximal" and "distal" are used relative to the medical professional, e.g. the proximal end is the end nearest the medical professional and the distal end is the part of the device that is inserted first into the patient.

Within the context of the invention, transcatheter includes percutaneous, trans-atrial, trans-femoral (through the leg), trans-apical (in the chest between the ribs), and trans-aortic (in the upper chest). Preferred embodiments are percutaneous systems, devices and methods.

BRIEF DESCRIPTION OF THE DRAWINGS

The invention will be further described with reference to the drawings and figures, in which:

FIG. 5A is a schematic representation of an outer view of an intracorporeal device without fixing means or control means.

FIG. 5B is a schematic representation of an internal view of the intracorporeal device without fixing means or control means.

FIG. 6A is a schematic representation of a cross section of an intracorporeal device utilising radial coupling between a motor and a motor coupling element.

FIG. 6B is a schematic representation of a cross section of an intracorporeal device utilising axial coupling between a motor and a motor coupling element.

DETAILED DESCRIPTION

The invention is described by way of examples, which are provided for illustrative purposes only. These examples should not be construed as intending to limit the scope of protection that is defined in the claims. For example, although various aspects have been described with respect to the heart and the circulatory system, this is not intended to be limiting, and is merely performed to provide an example of implementation. Aspects disclosed herein may be utilised in any medical device implantable within the human body, for example in the cardiovascular system, respiratory system, gastric system, neurological system, and the like, some examples including implantable pumps and drug delivery pumps. As used herein, the term "means" can be equivalently expressed as, or substituted with, any of the following terms: device, apparatus, structure, part, sub-part, assembly, sub-assembly, machine, mechanism, article, medium, material, appliance, equipment, system, body or similar wording.

Figure 1:
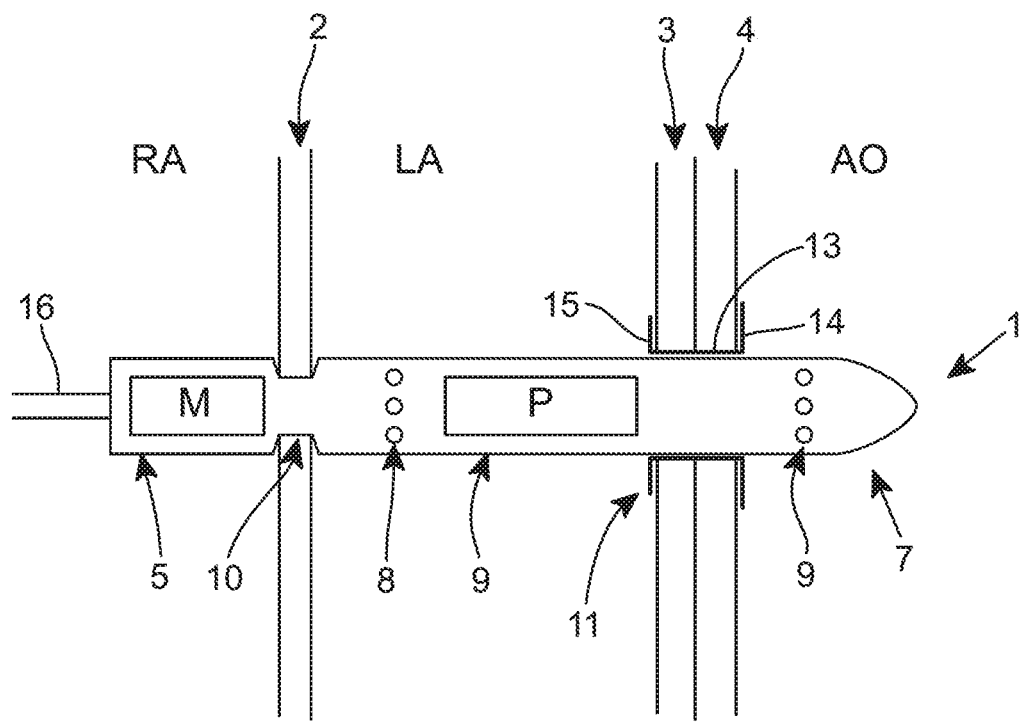
FIGS. 1, 1A, and 1B illustrate a method according to the present invention using a first intracorporeal device.

Referring to FIG. 1, there is illustrated a method according to the present invention for supporting heart function of a patient comprising the step of securing an intracorporeal device 1 across at least two anatomical walls of the heart, wherein at least one anatomical wall is an intra-cardiac wall and a least one anatomical wall is an extra-cardiac wall.

In this example, the intracorporeal device 1 is secured across the atrial septum 2 (an intra-cardiac anatomical wall), the roof of the left atrium 3 (an extra-cardiac anatomical wall) and the aortic wall 4 (i.e. a third anatomical wall). The intracorporeal device 1 comprises a proximal portion 5 located in use in the right atrium RA, an intermediary portion 6 located in use in the left atrium LA, and a distal portion 7 located in use in the aorta. A power and control cable 16 is coupled to an end of the proximal portion 5.

The intracorporeal device 1 is substantially cylindrical or comprises a substantially cylindrical housing. A motor M is located in the proximal portion 5 and a pump P is located in the intermediate portion 6. The position of the fluid inlet and outlet ports may be adjusted so that the fluid inlet ports are formed in the first fluid feeding compartment and the fluid outlet ports are formed in the second fluid receiving compartment. In this example, the fluid inlet ports 8 are formed in the intermediate portion 6 positioned in the left atrium LA and the fluid outlet ports 9 are formed in the distal portion 7 positioned in the aorta AO.

In an alternative implementation, the motor 5 may be housed in the intermediate portion 6. As a result, the proximal portion 5 is no longer required and is no longer situated in the right atrium. Thus only a power and control cable would be present in the right atrium.

Figure 1A:
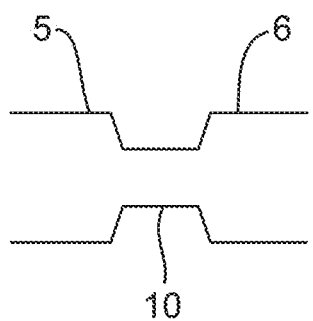
Figure 1B:
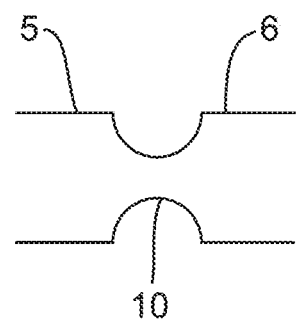

In FIG. 1, the intracorporeal device 1 comprises a circumferential recess 10 between its proximal and intermediate portions 5,6. The shape and dimensions of the recess are such that the atrial septum can be received into the recess 10. The recess 10 may have sloped or curved walls as shown in FIGS. 1A and 1B, respectively, to facilitate the insertion of the atrial septum 2 into the recess 10.

Where the intracorporeal device 1 is to be secured to a single anatomical wall (e.g. the atrial septum 2) then a recess 10 may be sufficient. However, when the intracorporeal device 1 is to be secured across two or more anatomical walls (e.g. the wall of the left atrium and the aortic wall 4), then a connector 11 may be preferred. The connector 11 shown in FIG. 1 is a separate connector.

Connectors suitable for use in the context of the present invention are described in detail in PCT/EP2017/050275, U.S. Ser. Nos. 15/288,642 and 15/288,738. The connector 11 generally comprises a neck 13 for fluid passage between two anatomical compartments, positioned in use across/through the anatomical walls 3,4; a first plurality of arms and/or blades 15 extending from the distal end of the neck 13 and lying in use against the wall of the receiving compartment and a second plurality of arms and/or blades 14 extending from the proximal end of the neck 13 and lying in use against the wall of the feeding compartment. The arms and/or blades are preferably integrally formed or secured to the distal end of the neck 13. In use, the arms and/or blades rest partially or wholly against the anatomical walls 3, 4. The neck 13 also supports the intracorporeal device 1 when it is positioned across the anatomical walls 3, 4. In use, (part of) the distal portion 7 on the intracorporeal device 1 is positioned through the neck 13 of the connector 11, and thus across the anatomical walls 3, 4. For example, the intracorporeal device may include a recess to receive the neck of the connector. The dimensions of the neck 13 and the distal portion 7 of the intracorporeal device 1 are arranged such that coupling the distal portion 7 with the neck 13 forms a pericardial space seal. Thus the neck 13 facilitates a seal as well as facilitating pump docking and support of the intracorporeal device 1.

Upon removal of the intracorporeal device from connector 11, the connector 11 forms a seal between the anatomical walls 3, 4 to prevent fluid diffusing between the two regions defined by said walls 3, 4.

This specific configuration secures the connector 11 to the anatomical walls 3,4 and enables the connector 11 to maintain the anatomical walls 3,4 in contact with each other while supporting the integrity of the anatomical walls 3,4. Thus the arms and/or blades act as tissue supporting members in order to support the integrity of the anatomical walls 3,4.

The intracorporeal device 1 may be provided with one or more recesses e.g. a circumferential recess to receive the neck 13 of the connector 11 therein.

Other means for securing the intracorporeal device 1 to the anatomical wall(s) 2,3, 4 are envisaged, including but not limited to tabs, hooks, arms, cushions, high friction surfaces, biologically active covering, and the like.

Figure 2:
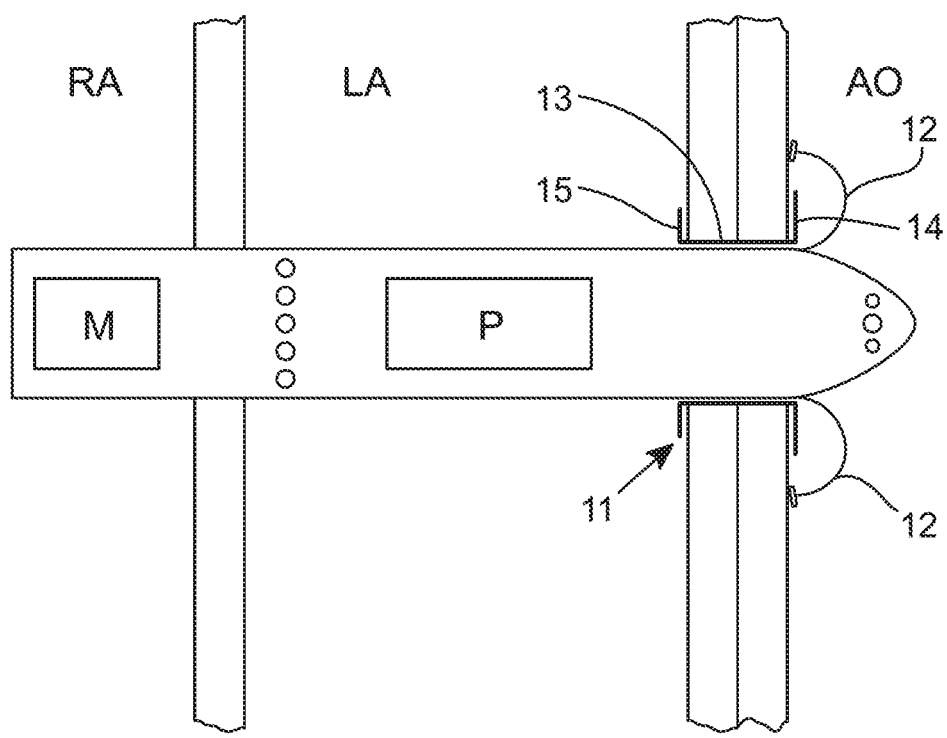
FIG. 2 illustrates a method according to the present invention using a second intracorporeal device.

Referring to FIG. 2, there is illustrated an alternative method of securing the intracorporeal device 1 with respect to the connector 11. Previously, referring to FIG. 1, the distal portion 7 of the intracorporeal device was coupled through/ to the neck 13 of the connector 11, e.g., via frictional force or through the compression of connector 11 (i.e. connector 11 is preferably made of an expandable/compressible material). Alternatively or in combination, a number of tissue support/fixing members 12 may be coupled to the distal portion 7 of the intracorporeal device 1. These tissue support/docking members 12, when deployed, contact the aortic wall and further support the intracorporeal device 1 with respect to the connector 11. Thus a combination of the connector 11 and the tissue support/docking members 12 enable enhanced support as well as the ability to easily couple and de-couple the distal portion 7 of the intracorporeal device 1 with respect to the connector 11.

Figure 3:
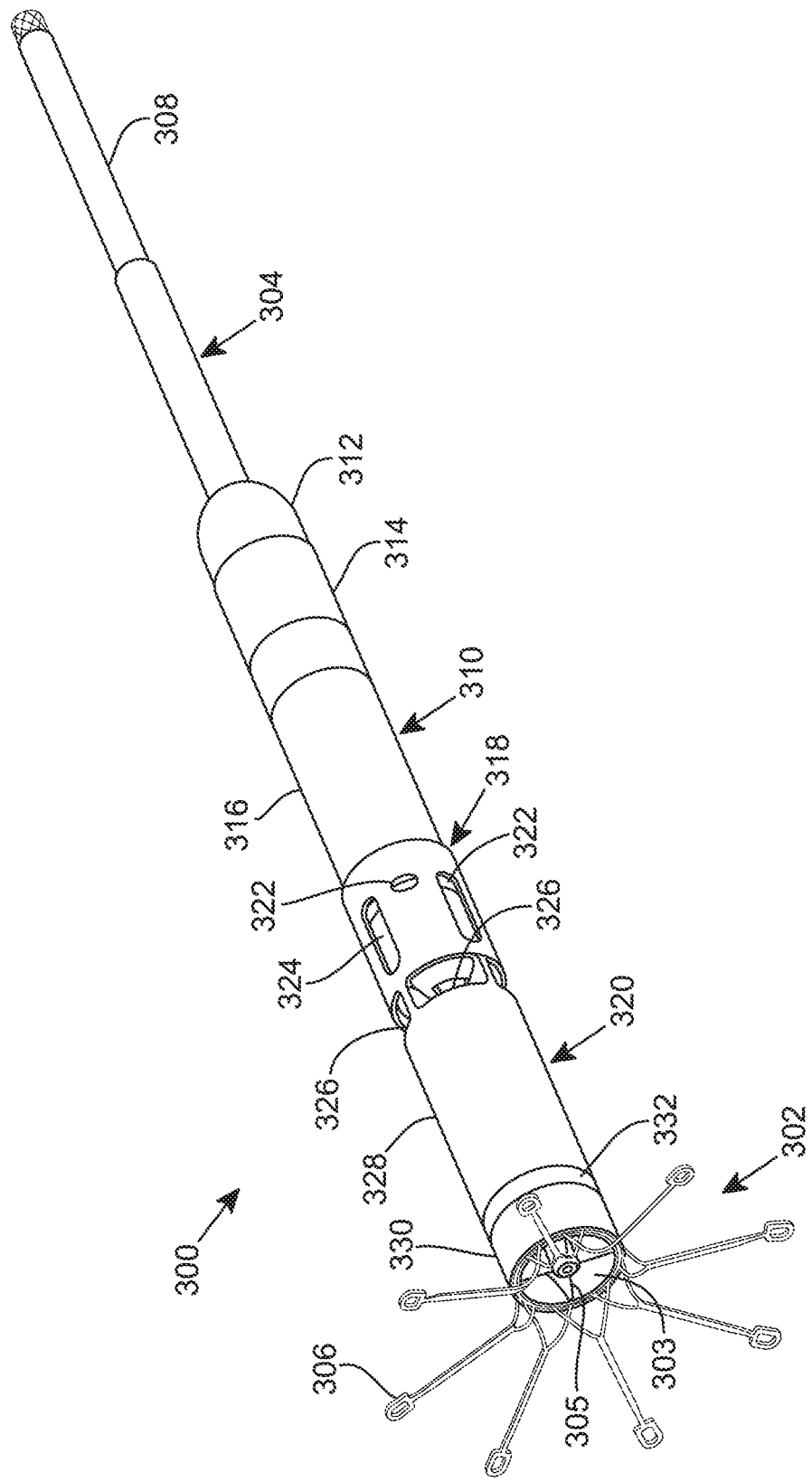
FIG. 3 is a schematic representation of an intracorporeal device incorporating fixing means and control means according to the present invention.

Referring to FIG. 3, there is illustrated a schematic representation of an intracorporeal device 300 with associated fixing means 302 and control means 304. The fixing means 302 in this embodiment relates to the tissue support/ docking members 12 described in relation to FIG. 2. The fixing means 302 comprise a coupler 330 attached to a proximal end of the fixing means 302. A number of pump docking members/support arms 306 are attached to a distal (opposite) end of the fixing means 302. FIG. 3 illustrates the fixing means 302 in a "deployed" position, wherein the number of pump docking members/support arms 306 are splayed out substantially perpendicular to the longitudinal axis of the intracorporeal device 300. These pump docking members/support arms 306, in use, abut a portion of the anatomical wall 4 (see FIG. 1,2), for example the aortic wall, in order to position and secure the intracorporeal device 300 between the anatomical walls 3, 4 (see FIG. 1,2) and inside the neck 13 of the connector 11.

The number of pump docking members/support arms 306 act as a tissue shield and pump protector, since the wall of the aorta is held away from the intracorporeal device 300 that is positioned inside the aorta. The number of pump docking members/support arms 306 distribute pressure so that each individual docking member/arm does not damage the anatomical wall 4.

If the intracorporeal device 300 needs to be removed from across the anatomical walls 3, 4, the pump docking members/support arms 306 are re-positioned into a "delivery" position, wherein the pump docking members/support arms 306 are arranged substantially parallel with the longitudinal axis of the intracorporeal device 300 to enable said device to be removed from the neck of the connector 11 (see FIG. 2). This has an advantage of allowing the intracorporeal device 300 to be removed without damaging the anatomical walls 3, 4, which are protected by the connector 11. On removal of the intracorporeal device 300, the connector 11 seals the space between the anatomical walls, 3, 4 until the intracorporeal device 300 is re-inserted.

In a preferred embodiment, the delivery of the intracorporeal device 300 is via echo guided trans-septal and/or trans-aortic methods for the specific puncture sites, wherein echo planes may be used for all puncture sites. An echo plane is a defined projection/view where anatomy and angles are predefined so as to visualise specific regions of interest in a specific way. The echo guided methods may be, for example, intra-cardiac, trans-esophageal, or trans-thoracic.

The coupler 330 is positioned over a crown connector/ coupling member (not visible) of the intracorporeal device 300 and abuts an end portion 332 of the intracorporeal device 300.

The control means 304 comprise a drive-line 308 that houses cabling to power and/or control the intracorporeal device 300. In this example, the control means 304 is coupled to a proximal portion 310 of the intracorporeal device 300 via a tapered portion 312. The tapered portion 312 tapers in size away from the proximal portion 310 of the intracorporeal device 300. The tapered portion 312 has an advantage of reducing strain on the connector interface (not shown) that is housed in portion 314 between the proximal portion 310 and the tapered portion 312. The connector interface couples the cabling in the control means 304 to the motor 316. The motor 316, connector interface and control means 304, form a hermetically sealed unit, which is arranged to prevent fluid ingress.

A portion of the motor 316 is situated within a rear portion 318 of the pump housing 320. The rear portion 318 of the pump housing 320 defines a number of washing holes 322, also called bore portions, that enable fluid, such as blood, to flow through the rear portion 318 of the pump housing and between a driving portion (not shown) of the motor 316 and a motor coupling element 324, which is partially visible in this figure. Fluid inlets 326 are arranged in the rear portion 318 of the pump housing 320. Between the fluid inlets 326 and the fixing means 302 is an impeller (not shown) situated within a front portion 328 of the pump housing 320.

The crown connector/coupling member (not shown) acts as a main outlet for fluid of the intracorporeal device 300. A static diffuser 305 (partially visible), inside of the crown connector/coupling member, interferes with the flow of fluid to generate a desired fluid flow out of the main outlet and into the aorta. The crown connector/coupling member comprises one or more fluid outlet ports 303.

In some other embodiments, for example the embodiment of FIG. 1, the fixing means 302 may be dispensed with. In these embodiments, the crown connector/coupling member may also be dispensed with. Thus the diffuser 305 may be situated within the distal end of the front portion 328 of the pump housing 320, rather than inside the crown connector/coupling member.

In this example, the distal portion of the intracorporeal device 300 comprises the fixing means 302 and crown connector/coupling member (not shown), wherein in use the distal portion is situated within the aorta. The intermediate portion of the intracorporeal device 300 comprises the pump housing 320 with its associated elements such as the impeller, and motor coupling element 324. The proximal portion of the intracorporeal device 300 comprises the portion of the motor that is not within the pump housing 320, the portion 314, tapered portion 312, and control means 304.

Figure 4:
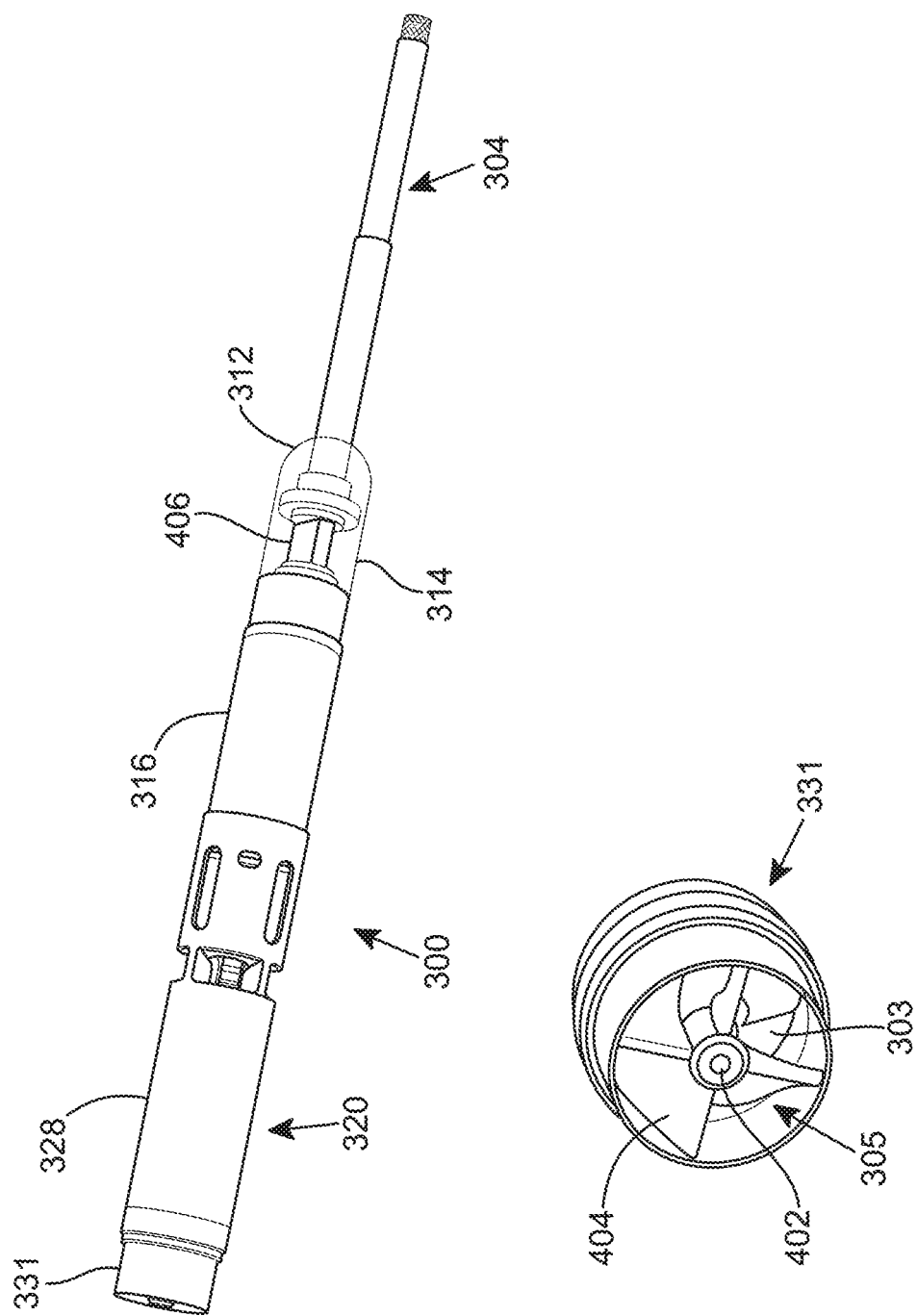
FIG. 4 is a schematic representation of the intracorporeal device from FIG. 3 without fixing means.

Referring to FIG. 4, the intracorporeal device 300 from FIG. 3 is illustrated without fixing means 302 coupled to the intracorporeal device. Thus in this example, the crown connector/coupling member 331 can be viewed in more detail. The crown connector 331 comprises the static diffuser 305 that is coupled to the side walls of the crown connector 331. The diffuser comprises static blades 404 and a guide wire holder 402. In use, fluid flows over the static blades 404 of the static diffuser 305, wherein the blades are orientated so to affect the orientation of fluid as it flows through the crown connector 331 to the one or more fluid outlet ports 303. The guide wire holder 402 also allows enhanced guide wire connectivity and/or balloon connectivity. For example, a guide wire (not shown) can be threaded through guide wire holder 402 to enable the intracorporeal device 300 to be accurately positioned within the human body via, for example, a catheter based implantation method.

In some examples, the crown connector 331 may be dispensed with and the static diffuser 305 may be positioned at a front portion 328 of the pump housing 320.

Referring again to FIG. 4, the portion 314 is illustrated so that connector interface 406 can be viewed. Connector interface 406 electrically couples the control means 304 to the back end of the motor. This enables power and/or control of the motor 316. Tapered portion 312 reduces strain on the connector interface 406. This is particularly important in the present invention because the intracorporeal device 300 needs to maintain flexibility. This is because in use the intracorporeal device 300 is implanted within the left and right atrium of the heart and the aorta via a catheter based insertion system. As such, the intracorporeal device needs to be flexible enough to follow the direction of the arterial system. Portion 314 maintains the hermetic seal of the motor 316, whilst allowing coupling of the control means 304 to the motor 316 so that the motor can be implanted within the circulatory system of the human body.

Referring to FIG. 5, there is illustrated a schematic representation of an intracorporeal device 500. In this example, power and control means are not illustrated. Further, in this example, the intracorporeal device 500 is illustrated without fixing means 302 or a crown connector/coupling member 331. Thus a diffuser 534 is situated at the outlet 503 of the intracorporeal device 500 rather than in the crown connector/coupling member 331, as illustrated in FIGS. 3 and 4.

Figure 5D:
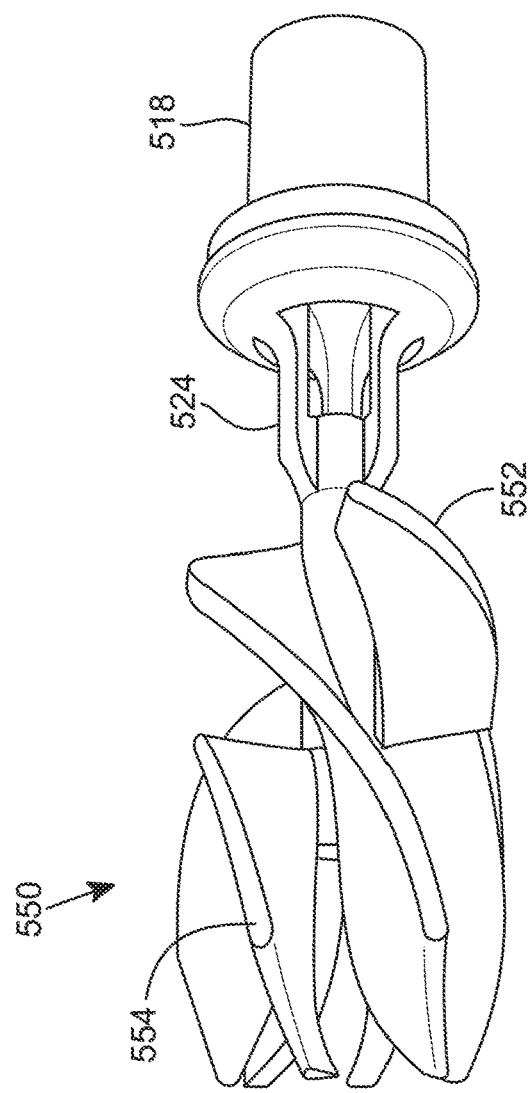
FIG. 5D is a schematic representation of an alternative impeller.
Figure 5C:
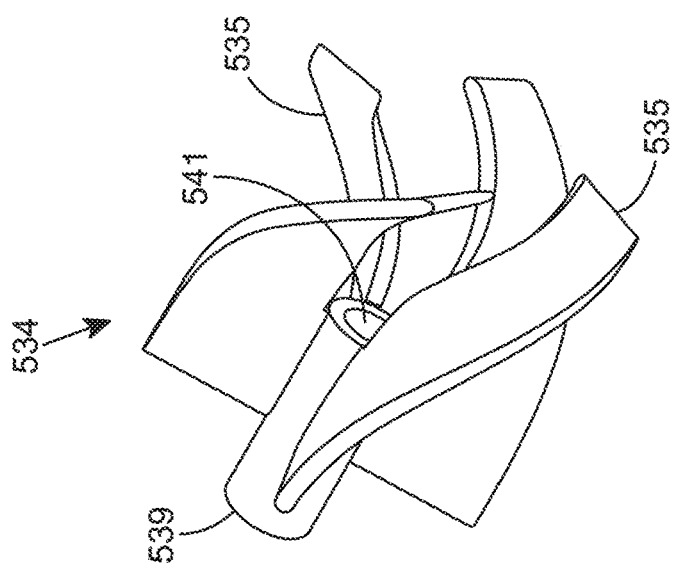
FIG. 5C is a schematic representation of a static diffuser utilised in the intracorporeal device in FIGS. 5A and 5B.

FIG. 5A illustrates an outer view of the intracorporeal device 500, whilst FIG. 5B illustrates an internal view of the intracorporeal device 500. FIG. 5C illustrates the diffuser 534 and FIG. 5D illustrates an alternative impeller design.

Intracorporeal device 500 in FIG. 5A comprises motor 502 and pump housing 504. A portion of the motor 502 is situated within the pump housing 504. The intracorporeal device in FIG. 5A comprises a proximal portion 506, an intermediate portion 508 and a distal portion 510, as discussed previously.

The portion of the pump housing 504 that contains the portion of the motor comprises a number of bore portions, which may also be washing holes/slits 512. Pump housing 504 further comprises a number of fluid inlets 514.

Referring to FIG. 5B, it can be seen that there is an interstitial space 516 between the motor 502 and a motor coupling element 518. The dotted line represents part of the motor 502 that extends inside the motor coupling element 518. In this example, this part relates to a hermetically sealed motor drive shaft 520. A bearing 522 couples the hermetically sealed motor drive shaft 520 to the motor coupling element 518. The hermetically sealed motor drive shaft 520 inside the motor coupling element 518 is of a smaller diameter than the motor coupling element 518, wherein the motor coupling element 518 is suspended around the hermetically sealed motor drive shaft 520 with the assistance of the bearing 522 and a magnetic field that is generated due to one or more magnetic elements on the motor drive shaft 520 and in the motor coupling element 518. In this example, the hermetically sealed motor drive shaft 520 inside of the motor coupling element 518 comprises a magnet or series of magnets (not shown) of a first polarity. The motor coupling element 518 comprises a magnet or series of magnets of a second polarity, wherein the first and second polarities are different. Thus an interstitial space is maintained between the portion of the hermetically sealed motor drive shaft 520 inside the motor coupling element 518 and the portion of the motor coupling element 518 that surrounds the hermetically sealed motor coupling element 518. This can be better understood from FIG. 6.

Magnetic coupling between the magnet on the motor drive shaft 520 and the motor coupling element 518 has an advantage that movement of the motor drive shaft 520 can be replicated by the motor coupling element 518 without the motor drive shaft 520 being exposed to fluid. Again, this feature can be better understood from FIG. 6. This allows the hermetic seal of the motor 502 to be maintained, allowing operation in a fluidic environment.

A further advantage of the magnetic coupling between the magnet on the motor drive shaft 520 and the motor coupling element 518 is that the motor 502, and any associated control means (not shown, see 304 from FIGS. 3 and 4), can be disconnected from the remainder of the intracorporeal device 500 when the device is situated within the body. Thus parts of the intracorporeal device 500 that are more likely to require removal, replacement, or modification, such as the motor 502 and cabling, can be removed and replaced, whilst keeping the pump housing 504 and associated elements such as the motor coupling element 518 in position in the body. This has an advantage of reducing movement and re-positioning of the pump housing 504, which may be positioned between anatomical walls of a patient's heart, such as the left and right atrium and aorta. Routine movement and/or re-positioning of the pump housing 504 with respect to the anatomical walls of a patient's heart may in some circumstances include risk of damage to said anatomical walls.

In this example, a number of segmented arms 524 surround the bearing 522. Interfaces of the segmented arms 524 couple the motor coupling element 518 to an impeller 526. Thus movement of the magnet on the motor drive shaft 520 can be translated to the impeller 526 without the drive shaft, or any other direct connection, of the motor 502 being coupled directly onto the impeller 526. The segmented regions between the arms 524 enable fluid to flow from the interstitial space 516 and to join fluid being forced through the impeller 526, via the segmented arms 524.

In another example, the segmented arms 524 may be replaced by one or more bore holes in the motor coupling element. The bore holes and segmented arms may collectively be referred to as bore portions.

There are several advantages of the arrangement of the motor 502 and the motor coupling element 518, which will now be discussed. During operation, the bearing 522 will generate heat as it supports movement of the motor coupling element 518 with respect to the hermetically sealed motor drive shaft 520. Fluid can flow through the interstitial space 516 between the motor 502 and the motor coupling element 518 to cool the bearing 522. The segmented arms 524, and/or bore holes, enable fluid to flow away from the bearing 522. Thus fluid can flow through washing holes 512 and into the interstitial space 516, cool the bearing 522 and mix with fluid being drawn into the impeller 530 via the fluid inlets 514. This enables cooling of the bearing 522, without the fluid increasing significantly in temperature to a point where it can become damaged. Without the segmented arms 524 or bore holes, fluid, such as blood, would not be able to easily flow past the bearing 522. Thus heat transferring from the bearing 522 to the fluid could cause the fluid to increase in temperature and become damaged. A two degree temperature rise in blood can cause blood damage and/or clotting. These clots could become dislodged and move around the circulatory system causing undesirable blockages.

In another example, the segmented arms 524 may be joined together to form a continuous arm. In this example, one or more bore holes may be present to enable fluid flow out of the motor coupling element 518.

Preferably the bearing 522 is formed from a ceramic material, which has an advantage of increased heat and wear tolerance as well as requiring less cooling. In turn, less heat is transferred to the fluid and thus reduces localised heating of the fluid and/or surrounding tissue.

As discussed above, the impeller 526 is coupled to the motor coupling element 518 via the segmented arms 524. In another example, wherein the segmented arms are joined together, the impeller is coupled to the motor coupling element 518 via the continuous arm.

During operation, the impeller 526 rotates about its axis 528 and draws fluid into the pump housing via the fluid inlet 514 and the segmented arms 524 (via the interstitial space 516). The impeller 526 comprises a body 530 and a number of blades 532. The blades 532 force fluid past the impeller 526 with respect to the pump housing at a rate defined by the rotational speed of the impeller 526.

Preferably, the body 530 of the impeller 526 is tapered, wherein the taper increases from the motor coupling element 518 end to a mid region of the impeller, before reducing again to an outlet end of the intracorporeal device 500. The tapered body is thus elliptical in shape with respect to the longitudinal axis of the impeller. The taper of the body 530 of the impeller 526 increases fluid pressure in the pump housing around the impeller 526. This results in fluid spending less time around parts of the motor 502 that generate heat, thereby reducing blood damage/clotting in and/or around the intracorporeal device 500.

In this example, the diffuser 534 is coupled to an outlet end of the impeller 526 via a bearing 536. The bearing 536 may be similar to bearing 522. The bearing 536 allows the impeller 526 to rotate about its axis whilst being supported by the diffuser 534. The diffuser 534 is coupled to the walls of the housing 504 so that it does not rotate. An end portion 538 of the diffuser 534 is positioned at the outlet 503 of the pump housing 504.

As illustrated in FIG. 5C, the diffuser 534 comprises a body 539, a number of blades 535 coupled to the body 539, and a guide wire holder 541. The guide wire holder 541 allows a guide wire and/or balloon to be coupled to the intracorporeal device 500. Preferably, the diffuser comprises four blades 535. The blades 535 vary in thickness and orientation with respect to the body 539 of the diffuser 534. The blades 535 curve away from or towards the body 539. The thickness of the blades 535 varies as the blades 535 move away from the body 539 of the diffuser. The thick/thin profile of the blades 535 coupled with the angle of the blades 535, allows optimal diffusion of fluid from the outlet of the intracorporeal device 500. Thus the thickness profile and the angle of the blades 535 are optimised to minimise blood damage and maximise pressure generation inside the intracorporeal device 500.

A general operation of the intracorporeal device 500 will now be given. The hermetically sealed motor drive shaft 520 rotates about its longitudinal axis, resulting in magnet(s) on the motor drive shaft and the magnet(s) on the motor coupling element 518 also rotating with respect to each other, which in turn rotates the impeller 526 about its longitudinal axis, whilst the diffuser 534 remains in a fixed position. In use, the proximal portion 506 is positioned in the right atrium. The intermediate portion 508, comprising the washing holes/slits 512 and the fluid inlets 514 are positioned in the left atrium. The distal portion comprising the outlet of the intracorporeal device 500 is positioned in the aorta. Thus the pump housing 504 is positioned between the wall of the left atrium 3 and the aortic wall 4 (see FIG. 1). A connector 11 seals the wall of the left atrium 3 and the aortic wall 4 around the pump housing 504, effectively providing a fluid seal. Thus fluid, such as blood, can only flow between the wall of the left atrium 3 and the aortic wall 4 via the intracorporeal device 500 when the device is operating at full capacity. Impeller 530 draws fluid into pump housing 504 via the fluid inlets 514, the interstitial space 516 and associated segmented arms 524. Fluid pressure builds up in the pump housing 514 due to the tapered design of the body 530 of the impeller 526. The impeller blades 532 generate an axial fluid flow through the impeller 526, wherein the diffuser 534 optimally provides a flow/diffusion of fluid to the outlet of the pump housing 504 and into the aorta. As discussed previously, the length of the pump housing 504 and constituent components are designed such that the one or more fluid inlet ports are in the left atrium and the one or more fluid outlet ports are in the aorta.

In an example, wherein the intracorporeal device 500 is operating at partial capacity, for example to provide partial support to a patient's heart, there may be a partial flow of fluid, such as blood, through the left ventricle.

Referring to FIG. 5D, an alternative impeller 550 is illustrated. In this example, the alternative impeller, denoted the "mixed flow" impeller 550 is illustrated coupled to the motor coupling element 518 via the segmented arms 524. The mixed flow impeller 550 comprises a first set of blades 552 and a second set of blades 554, wherein the first set of blades 552 are longer than the second set of blades 554. The distribution of different shaped and angled blades gives the mixed flow impeller 550 a partial radial outlet, as well as an axial outlet. Thus the mixed flow impeller generates an axial as well as a radial flow of fluid towards the outlet of the intracorporeal device 500. This has an advantage of increasing efficiency of the intracorporeal device 500 as the mixed flow impeller 550 provides higher output pressure compared to axial flow impellers. A further advantage of the mixed flow impeller 550 is that an intracorporeal device 500 utilising this impeller 550, as opposed to the impeller 530, has a reduced overall length because there is no need for the diffuser 534.

Optionally, a diffuser that similar to diffuser 534 may also optionally be coupled to the mixed flow impeller 550.

FIG. 6A illustrates a schematic representation of radial coupling between the motor and motor coupling element that may be utilised in the intracorporeal device, and FIG. 6B illustrates a schematic representation of axial coupling between the motor and motor coupling element that may be utilised in the intracorporeal device. Both FIGS. 6A and 6B include a diffuser 634 between a main outlet of the intracorporeal device 600, 650 and the impeller 632. Thus fixing means 302 and crown connector/coupling member 331 are not illustrated.

Referring to FIG. 6A, a cross section of an intracorporeal device 600 is illustrated. Motor 602 includes a motor drive shaft 604 that extends into a portion of the motor that is partially surrounded by a motor coupling element 606. An end of the shaft 604 includes a first set of magnets 608 of a first polarity. The first set of magnets 606 are housed in a hermetically sealed unit 610 that encapsulates the magnet 606 and drive shaft. The motor coupling element 606 partially surrounds the hermetically sealed unit 610, wherein a second set of magnets 615 of an opposing polarity are situated within the motor coupling element 606. A bearing 612 rotatably couples the motor coupling element 606 to the hermetically sealed unit 610. The opposing magnetic fields generated by the first set of magnets 608 and the second set of magnets 615 attract each other, and thus pull the motor coupling element 606 towards the hermetically sealed unit 610. Magnets surround the full circumference of the hermetically sealed unit 610 and the motor coupling element 606 such that there is an equal magnetic force that prevent any interfaces of the hermetically sealed unit 610 and motor coupling element 606 from touching, thereby generating an interstitial space between the hermetically sealed unit 610 and the motor coupling element 606. In use, fluid, for example blood, flows into interstitial space 614 between the motor 602 and the motor coupling element 606 and through the interstitial space defined by the hermetically sealed unit 610 and the motor coupling element 606 and exits via the gaps between the segmented arms 616. Thus the bearing 612 is "washed" with fluid, which prevents the bearing 612 from generating excessive heat. Due to the flow of fluid from the interstitial space 614 to the segmented arms 616, the bearing 612 does not generate localised heating or heat the fluid as it "washes" the bearing 612.

Additionally, fluid flows 617 into fluid inlets 618 and mixes with fluid 619 exiting between the segmented arms 616. As discussed previously, the segmented arms 616 may be replaced by a continuous arm having one or more bore holes to achieve the same fluid flow effect.

In this example, the magnet 608 on the drive shaft 604 rotates along the axis of the shaft 604, resulting in an associated rotation of the magnet 615 in the motor coupling element 606. This radial coupling eliminates axial forces in the coupling assembly and has a higher rated torque compared to an axially coupled device (discussed in FIG. 6B). Furthermore, the bearing 612 experiences less friction compared to an axially coupled device.

Referring to FIG. 6B, a cross section of an axially coupled intracorporeal device 640 is illustrated, comprising a motor housing part 650 and a pump part 651. In this example, a first magnet 652 of a first polarity is arranged on an end of motor shaft 654 within the motor housing part 650. A second magnet 656 of a second different polarity is positioned opposite the first magnet in the pump part 651, wherein movement of the shaft 654 and thus the first magnet 652 is replicated by the second magnet 656. This form of coupling is defined as axial coupling.

An interstitial space 670 is defined between the motor housing part 650 and the pump part 651, similar as discussed with respect to FIG. 6A. The interstitial space allows fluid to flow 671 around a bearing 672 that supports the pump part 651 with respect to the motor housing part 650.

Axial coupling is simpler in design than radial coupling illustrated in FIG. 6A. This form of indirect coupling maintains a hermetic seal of the motor and allows torque transfer between the motor and impeller drive shaft 658. Further, axial coupling is simpler to manufacture because the magnetic elements are not as thin as the magnetic elements needed for radial coupling.

Figure 7:
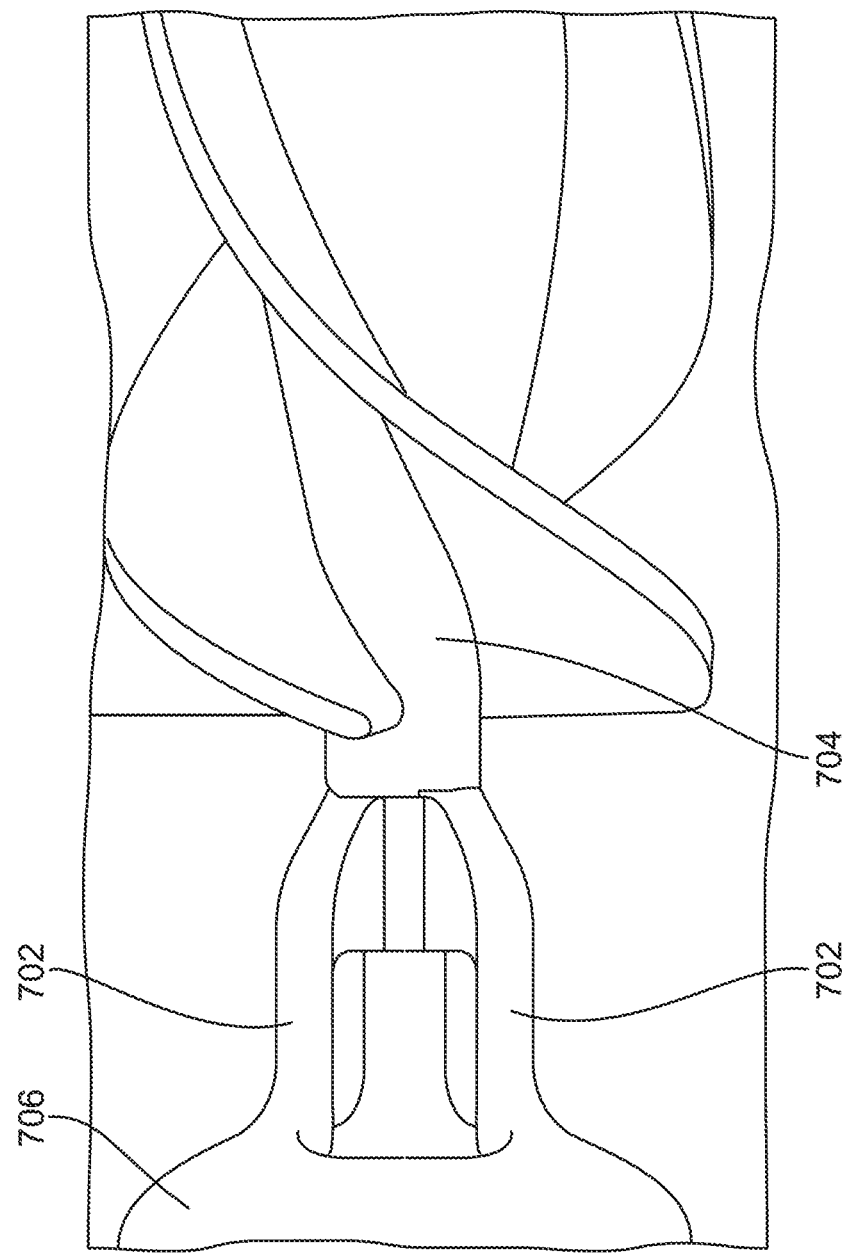
FIG. 7 is a schematic representation of segmented arms from the motor coupling element.

Referring to FIG. 7, an example of the segmented arms from FIG. 6 are illustrated. Segmented arms 702 couple the impeller 704 to the motor coupling element 706. The regions/gaps between the segmented arms 702 allow fluid to flow past and "wash" the bearing (not shown). Thus fluid can flow in the interstitial space between the hermetically sealed motor drive shaft (not shown) and the motor coupling element 706. This has an advantage of cooling the device and maintaining a flow of fluid to prevent damage and/or clotting. The fluid that is output from the gaps in the segmented arms 702 mixes with the fluid drawn into the pump housing (not shown) during rotation of the impeller. The combined fluid flows through the impeller 704 in an axial manner.

Figure 8:
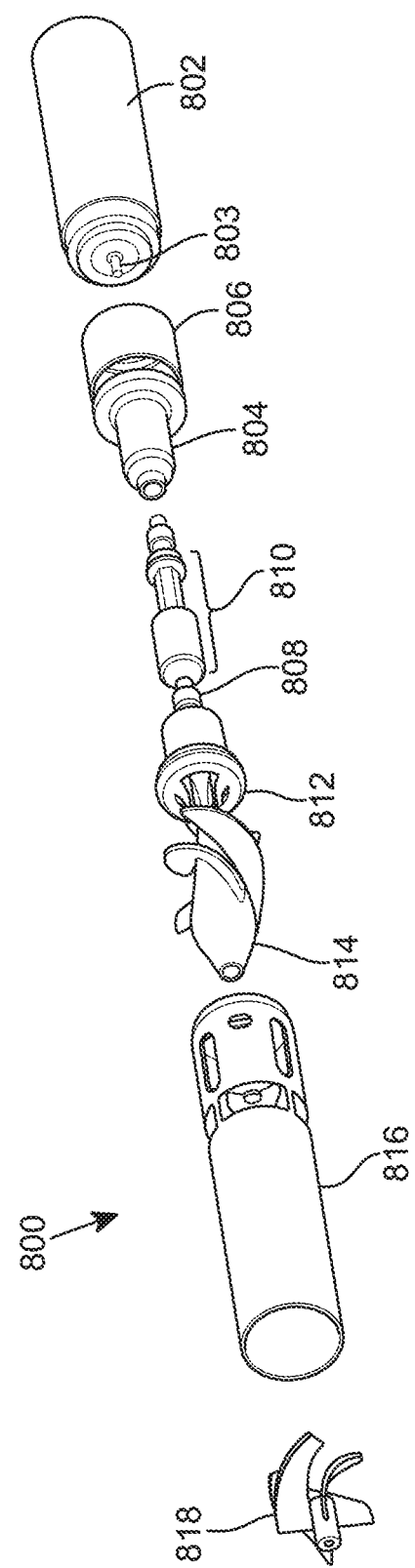
FIG. 8 is an exploded schematic representation of constituent elements of an intracorporeal device.

Referring to FIG. 8, an exploded view of an intracorporeal device 800 is illustrated. The separate features will be put into context using the described components in FIGS. 6A and 6B.

Motor 802 comprises motor shaft 803, wherein the motor shaft 803 is housed inside hermetically sealed unit 804 and sealing conduit 806. The hermetically sealed unit 804 corresponds to the hermetically sealed unit 610 from FIG. 6A. The hermetically sealed unit 804 is hollow to enable the motor shaft 803 and magnet (not shown) to rotate within the hermetically sealed unit. The sealing conduit 806 houses the hermetically sealed unit 804 and part of the motor coupling element 812. In this example, the sealing conduit 806 provides the gaps 614 in FIG. 6A to enable fluid to enter the void between the motor coupling element 606 and the hermetically sealed unit 610 from FIG. 6A.

Bearing 808 relates to bearing 612 from FIG. 6A, and is positioned such that it rotatably couples the hermetically sealed unit 804 to the motor coupling element 812, thereby enabling rotation of the motor coupling element 812 about the bearing 808 axis. Magnetic components 810 relate to the second magnet 615 situated within the motor coupling element 606 from FIG. 6A. The magnetic components 810 are fixably attached to the motor coupling element 812 so that movement of the magnet within hermetically sealed unit 804 is translated to the motor coupling element 812. Impeller 814 is coupled to the motor coupling element 812 so that movement of the magnet within the hermetically sealed unit 804 is also translated to the impeller 814. Diffuser 818 is coupled to the impeller 814 via a bearing (not shown) and to the pump housing 816. The impeller 814 rotates about its longitudinal axis, whilst the diffuser 818 remains fixed. Pump housing 816 is positioned around components as illustrated with respect to FIG. 6A.

Optionally, the bearings discussed above, for example bearing 808, may be hydraulic bearings, or a combination of ceramic and hydraulic bearings, wherein the base of the bearing (motor side) may be ceramic and the top of the bearing (outlet side) may be hydraulic.

Optionally, the diffuser 818 may be positioned in a crown connector/coupling member (not shown), such as the crown connector 331 from FIG. 3

Although the present invention has been described with respect to a left atrium to aorta procedure, the system and method can also be applied to other delivery sites including, but not limited to, right atrium-aorta, vena cava-pulmonary artery, vena cava-aorta. Thus, the present invention can be broadly applied for example as left ventricular assist devices (LVAD), right ventricular assist devices (RVAD) or biventricular assist devices (BiVAD), for cardiopulmonary support (CPS) or for intra-corporeal membrane oxygenation (ICMO) or bubble oxygenation, for the treatment of other organs with pressure issues (e.g. gastric or neurological procedures). The present invention is versatile and a wide variety of applications can therefore be envisaged.

Thus, from the above description, it can be seen that the present invention provides a connector for establishing fluid communication between two anatomical compartments. The connector also enables a pump or other medical devices to be securely implanted across one or more anatomical walls. This can be achieved accurately and safely. The present invention provides a device which can establish fluid communication with minimal risk of blood leakage during the implantation procedure, and whilst providing support to the anatomical walls and tissues so as to prevent injury to the patient.

The invention claimed is:

1. An intracorporeal device for supporting heart function of a patient, wherein said intracorporeal device is configured to be secured across at least two intra-cardiac anatomical walls of the heart,
   further comprising a proximal portion positioned in a first anatomical compartment, an intermediate portion positioned in a second anatomical compartment, a distal portion positioned in a third anatomical compartment.

2. The intracorporeal device according to claim 1, wherein the intracorporeal device is further configured to be secured across an extra-cardiac anatomical wall.

3. The intracorporeal device according to claim 1, wherein the intracorporeal device is configured to be secured to one or more anatomical walls by means of:
   a connector, said connector arranged to be positioned across said one or more anatomical walls; and, optionally,
   a fixing means, said fixing means being integrally formed or coupled to the intracorporeal device.

4. The intracorporeal device according to claim 3, wherein the fixing means comprises a plurality of arms extending from the intracorporeal device.

5. The intracorporeal device according to claim 1, wherein the intracorporeal device comprises one or more recesses adapted and configured to receive one or more anatomical walls.

6. The intracorporeal device according to claim 1, comprising a motor located in the proximal portion, one or more fluid inlet ports in the intermediate portion, a pump in the intermediate portion, and one or more fluid outlet ports in the distal portion.

7. The intracorporeal device according to claim 6, wherein the pump comprises an impeller and a pump housing, wherein the impeller is positioned within the pump housing.

8. The intracorporeal device according to claim 7, wherein the impeller comprises a tapered profile that is at a maximum at a central portion of the impeller.

9. The intracorporeal device according to claim 6, comprising a static diffuser positioned in the distal portion and prior to the one or more fluid outlet ports.

10. The intracorporeal device according to claim 1, comprising a coupling member at an end of the distal portion.

11. The intracorporeal device according to claim 10, wherein the coupling member comprises a static diffuser.

12. The intracorporeal device of claim 10, wherein the coupling member facilitates coupling of a fixing means.

13. The intracorporeal device according to claim 9, wherein the static diffuser is positioned between the impeller and the one or more fluid outlet ports.

14. The intracorporeal device according to claim 6, comprising a motor coupling element that is arranged to couple a drive shaft of the motor to the pump.

15. The intracorporeal device according to claim 14, wherein the motor coupling element magnetically couples the drive shaft of the motor to the pump.

16. The intracorporeal device according to claim 15, wherein the motor coupling element axially couples the drive shaft of the motor to the pump.

17. The intracorporeal device according to claim 15, wherein the motor coupling element radially couples the drive shaft of the motor to the pump.

18. The intracorporeal device according to claim 14, wherein the motor, the drive shaft and a magnetic element at an end of the drive shaft are situated in a hermetically sealed housing.

19. The intracorporeal device according to claim 18, wherein a portion of the motor coupling element surrounds a portion of the hermetically sealed housing containing the magnetic element.

20. The intracorporeal device according to claim 19, wherein an interstitial space is present between the portion of the motor coupling element and the portion of the hermetically sealed housing.

21. The intracorporeal device of claim 14, wherein an interface of the motor coupling element is magnetically fixable to an interface of the motor in order to couple the drive shaft to the pump, and wherein a gap is present between the interfaces during coupling.

22. The intracorporeal device according to claim 21, wherein in use the gap facilitates fluid flow between the motor interface and the interface of the motor coupling element.

23. The intracorporeal device according to claim 21, wherein a further interface of the motor coupling element couples to an interface of the impeller.

24. The intracorporeal device according to claim 14, wherein the motor coupling element comprises one or more bore portions.

25. The intracorporeal device according to claim 24, wherein the one or more bore portions comprise bore holes that extend through the motor coupling element.

26. The intracorporeal device according to claim 24, wherein the one or more bore portions comprise segmented arms that couple said interfaces of the motor coupling element to the respective impeller interfaces.

27. The intracorporeal device according to claim 24, wherein in use fluid is arranged to flow between the motor interface and the interface of the motor coupling element and through the one or more bore portions towards the impeller.

28. The intracorporeal device according to claim 24, wherein the one or more fluid inlet ports are positioned between the one or more bore portions and the impeller.

29. The intracorporeal device according to claim 6, wherein the motor comprises power and control means.

30. The intracorporeal device according to claim 29, wherein the power and control means is coupled to the motor via a tapered portion.

* * * * *